United States Patent
Wang et al.

(10) Patent No.: US 7,634,325 B2
(45) Date of Patent: Dec. 15, 2009

(54) PREDICTION OF UNIFORMITY OF A WAFER

(75) Inventors: Jean Wang, Hsin Ch (TW); Francis Ko, Taichung (TW); Ping-Hsu Chen, Hsinchu (TW); Henry Lo, Hsinchu (TW); Chih-Wei Lai, Hsinchu (TW)

(73) Assignee: Taiwan Semiconductor Manufacturing Company, Ltd., Hsin-Chu (TW)

( * ) Notice: Subject to any disclaimer, the term of this patent is extended or adjusted under 35 U.S.C. 154(b) by 88 days.

(21) Appl. No.: 11/744,107

(22) Filed: May 3, 2007

(65) Prior Publication Data
US 2008/0275588 A1 Nov. 6, 2008

(51) Int. Cl.
*G06F 19/00* (2006.01)
(52) U.S. Cl. .................. 700/121; 700/303; 438/14; 716/4
(58) Field of Classification Search .............. 700/121; 438/680, 14, 16–17; 716/4
See application file for complete search history.

(56) References Cited

U.S. PATENT DOCUMENTS

| | | | |
|---|---|---|---|
| 4,493,745 A | 1/1985 | Chen et al. | |
| 5,402,367 A | 3/1995 | Sullivan et al. | |
| 5,503,707 A | 4/1996 | Maung et al. | |
| 5,838,595 A | 11/1998 | Sullivan et al. | |
| 6,211,094 B1 * | 4/2001 | Jun et al. | 438/758 |
| 6,254,457 B1 | 7/2001 | Perrin et al. | |
| 6,582,976 B2 | 6/2003 | Watanabe | |
| 6,623,333 B1 | 9/2003 | Patel et al. | |
| 6,645,781 B1 | 11/2003 | Jiang et al. | |
| 6,917,849 B1 * | 7/2005 | Pasadyn et al. | 700/121 |
| 6,961,626 B1 * | 11/2005 | Paik | 700/31 |
| 7,144,297 B2 | 12/2006 | Lin et al. | |
| 2008/0032426 A1 * | 2/2008 | Michaelson et al. | 438/7 |

FOREIGN PATENT DOCUMENTS

| | | |
|---|---|---|
| EP | 0445640 A2 | 9/1991 |
| EP | 0643344 A1 | 7/1993 |

OTHER PUBLICATIONS

Ling, Zhi-min et al., "In-Line Supervisory Control In A Photolithographic Workcell", Advanced Techniques for Integrated Circuit Processing, 1990, pp. 660-669, SPIE vol. 1392.

Dishon, G. et al., "Monitoring Choices Of CMP Planarization Processes", CMP-MIC Conference, Feb. 1997, pp. 391-398.

* cited by examiner

*Primary Examiner*—Kidest Bahta
*Assistant Examiner*—Nathan Laughlin
(74) *Attorney, Agent, or Firm*—Haynes and Boone, LLP (57) ABSTRACT

A method of monitoring uniformity of a wafer is provided. A wafer parameter is selected. Manufacturing data is collected. The manufacturing data includes measurements of the selected wafer parameter. An average offset profile of the wafer parameter for a first and second wafer is determined using the manufacturing data. The first and second wafer are associated with a product type and were processed by a processing tool. An offset profile for a third wafer is predicted for a wafer using the average offset profile. The third wafer is associated with the product type and was processed by the processing tool.

18 Claims, 9 Drawing Sheets

PREDICTION OF UNIFORMITY OF A WAFER

CROSS REFERENCE

The present disclosure is related to the commonly-assigned U.S. Pat. No. 7,144,297, entitled "METHOD AND APPARATUS TO ENABLE ACCURATE WAFER PREDICTION," the entire disclosure of which is hereby incorporated by reference.

BACKGROUND

The present disclosure relates generally to semiconductor fabrication, and more particularly, to prediction of the uniformity of a wafer.

Semiconductor integrated circuits substrates such as wafers are fabricated using a plurality of wafer fabrication processes. The fabrication processes, including the processing tools necessary to perform the process, are monitored and controlled to maintain integrated circuit quality and yield. As integrated circuits reduce in size and increase in complexity, the need for monitoring various aspects of the wafer may increase. However, increased monitoring is costly in cycle time and manpower, and requires that additional metrology tools be available. One such potentially costly monitoring need includes measuring a wafer parameter at several locations on a wafer to determine the uniformity of the wafer. Wafer uniformity may vary as wafer parameters may vary, for example from the center to the edge of the wafer or from one segment of the wafer to another due to variations in the fabrication processes. Understanding the uniformity of a wafer may be important to maintaining quality, reliability, and yield standards for the wafer.

Accordingly, it would be desirable to provide for predicting the uniformity of a wafer.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

FIG. 3b is a graph illustrating an embodiment of the method of FIG. 3a.

FIG. 3c is a graph illustrating an embodiment of the method of FIG. 3a.

FIG. 3d is a graph illustrating an embodiment of the method of FIG. 3a.

FIG. 3e is a graph illustrating an embodiment of the method of FIG. 3a.

FIG. 3f is a graph illustrating an embodiment of the method of FIG. 3a.

DETAILED DESCRIPTION

The present disclosure relates generally to the fabrication of semiconductor devices, and more particularly, predicting a value of a wafer parameter at a location on the wafer which may be helpful in determining wafer uniformity. It is understood, however, that specific embodiments are provided as examples to teach the broader inventive concept, and one of ordinary skill in the art can easily apply the teaching of the present disclosure to other methods or apparatus. Also, it is understood that the methods and apparatus discussed in the present disclosure include some conventional structures and/or processes. Since these structures and processes are well known in the art, they will only be discussed in a general level of detail. Furthermore, reference numbers are repeated throughout the drawings for sake of convenience and example, and such repetition does not indicate any required combination of features or steps throughout the drawings.

Figure 1:
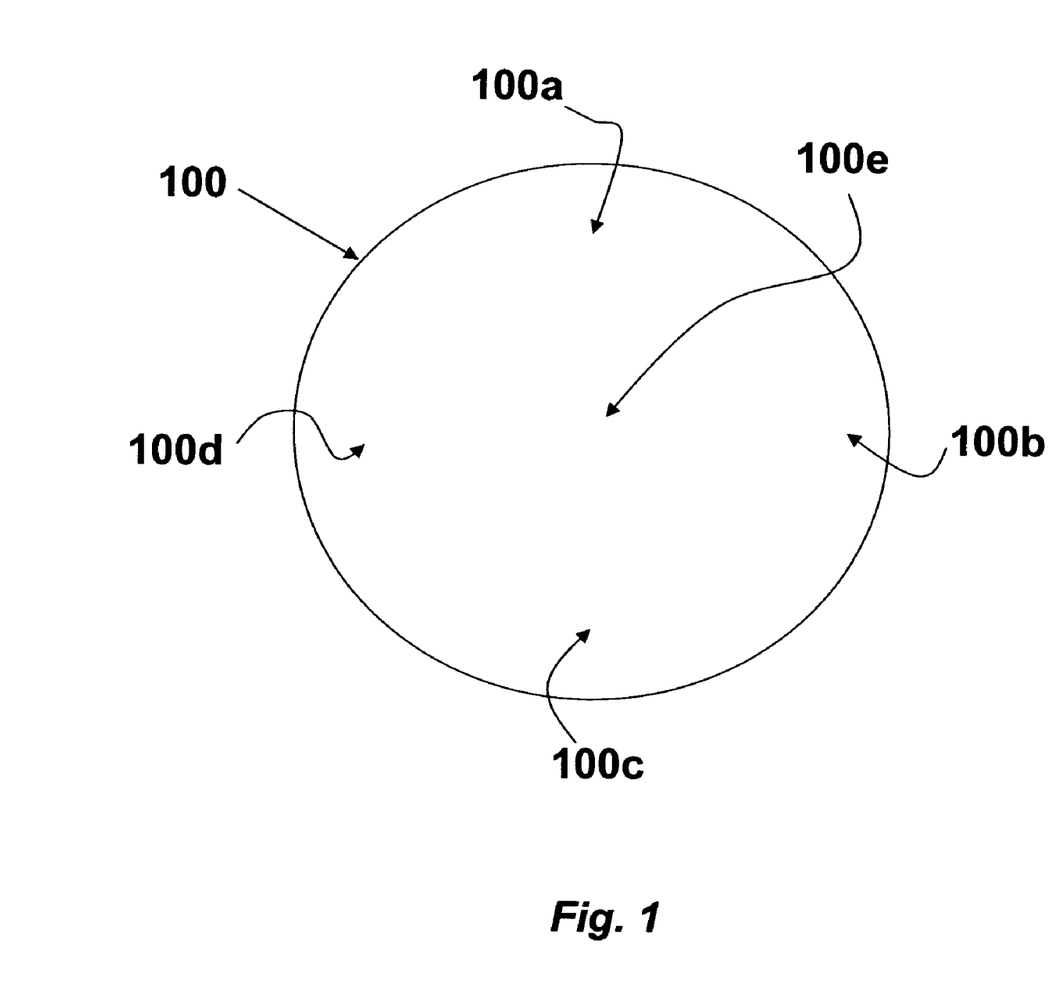
FIG. 1 is a schematic view illustrating an embodiment of a wafer.

Referring to FIG. 1, a wafer 100 is one example of an item that can benefit from one or more embodiments of the present invention. In the present example, the wafer 100 is a semiconductor wafer that is either in the middle of fabrication, or has completed fabrication. The wafer 100 may be fabricated using processes such as chemical vapor deposition (CVD), physical vapor deposition (PVD), etch processes, thermal oxidation, ion implantation, chemical mechanical polishing (CMP), rapid thermal annealing (RTA), photolithography, and/or a variety of other fabrication processes known in the art. The wafer 100 may be associated with a product type. A wafer associated with a product type may produce, upon completion of the fabrication process, integrated circuits of the product type. During fabrication, the wafer 100 may be monitored by electrical, optical, and/or analytical tools to determine the uniformity of the wafer. A plurality of locations 100a, 100b, 100c, 100d, and 100e are illustrated on the wafer 100. The uniformity of the wafer 100 may include the values of a wafer parameter at the locations 100a, 100b, 100c, 100d, and/or 100e. A wafer parameter may include, for example, the dimensions of a feature including a critical dimension or thickness of a layer, reflectivity, resistivity, and/or sheet resistance. In an embodiment, the determination of the uniformity of the wafer 100 includes the determination of the value of a wafer parameter at additional, fewer, and/or different locations than illustrated. In an embodiment, the value of a wafer parameter at one location such as, the location 100e, is different than the value of a wafer parameter a second location such as, the location 100c. In an embodiment, the wafer 100 is included in a lot, or batch, of wafers. The lot of wafers may include wafers associated with the same product type and that are processed at substantially the same time.

Figure 2:
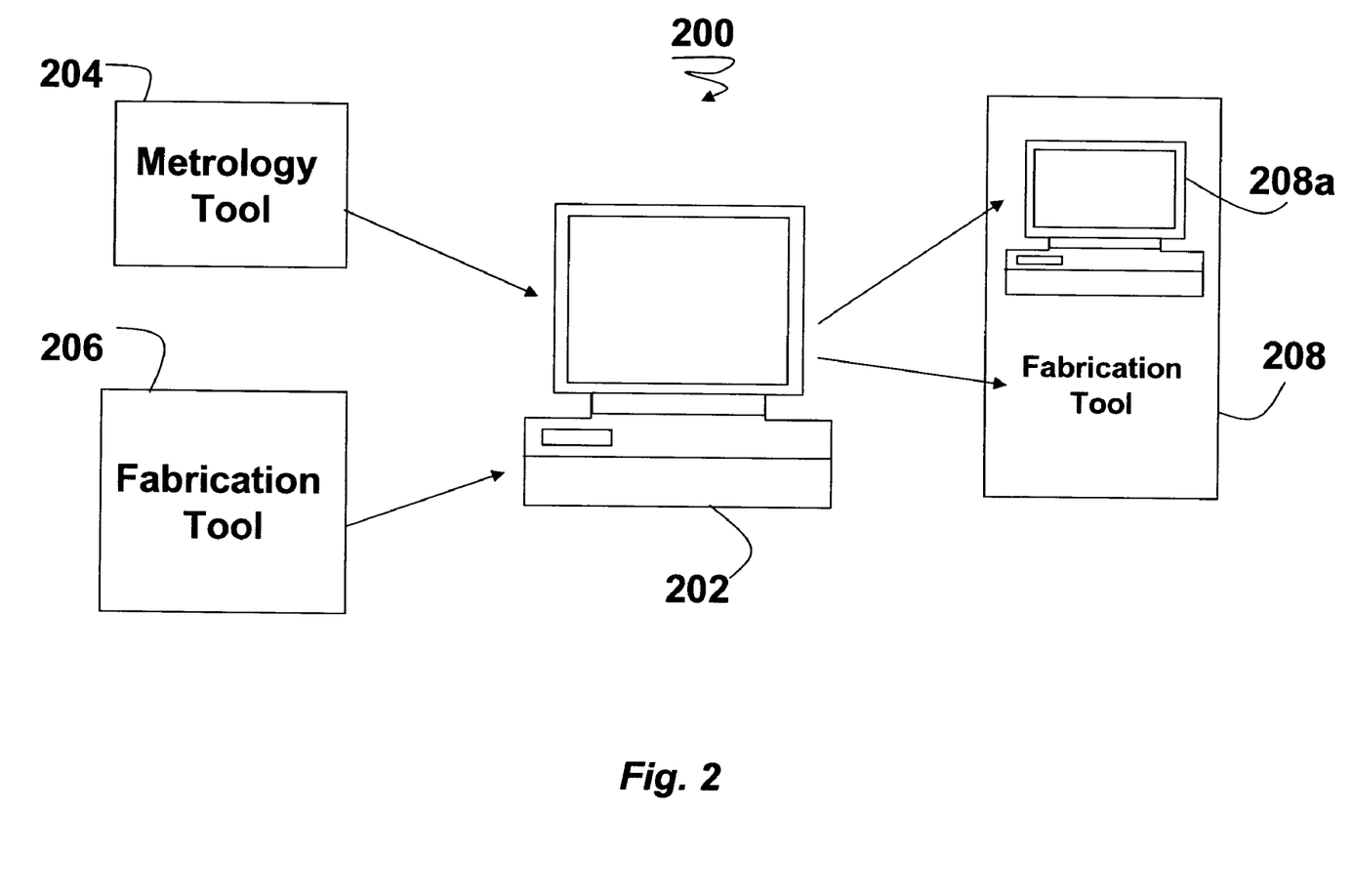
FIG. 2 is a schematic view illustrating an embodiment of a system for predicting the uniformity of a wafer.

Referring now to FIG. 2, a system 200 operable to determine the uniformity of a wafer such as the wafer 100, described above with reference to FIG. 1, is illustrated. The system 200 includes a metrology tool 204, a first fabrication tool 206, a computer 202, and a receiving fabrication tool 208, which is associated with a receiving computer 208a. In an embodiment, the receiving computer 208a is be a part of the receiving fabrication tool 208 and may perform or assist in the fabrication to be done by the tool 208. In another embodiment, the receiving computer 208a is connectable to the receiving fabrication tool 208 over a link and/or network.

In an embodiment, the metrology tool 204 may include microscopes, micro-analytical tools, line width measurement tools, particle distribution tools, surface analysis tools, resistivity and contract resistance measurement tools, mobility and carrier concentration measurement tools, junction depth measurement tools, film thickness measurement tools, and/or a variety of other metrology tools known in the art. In an embodiment, the fabrication tool 206 may be a CVD tool, a PVD tool, an etch tool, a thermal oxidation tool, an ion implantation tool, photolithography tool, and/or a variety of other processing tools known in the art.

The computer 202 is operable to perform actions including manipulating information, receiving information, storing information, and/or transferring information. The computer may include a processor and/or memory for implementing and/or storing computer instructions consistent with the steps and methods discussed in greater detail below. In an embodiment, the computer 202 includes multiple computers. In an embodiment, the computer 202 includes equipment or code embedded in a processing tool such as the fabrication tool 206. In the illustrated embodiment, the computer 202 is connected to and receives information from the metrology tool 204. In the illustrated embodiment, the computer 202 is further connected to and receives information from the fabrication tool 206. In an embodiment, the computer 202 is connected to and receives information from additional sources. In an embodiment, the information received from the fabrication tool 206 and the metrology tool 204 includes manufacturing data. Manufacturing data may include tool data and wafer data. Tool data includes process parameters and may be passed from the fabrication tool 206. In an embodiment, the tool data includes a process parameter for a wafer that identifies a processing tool used to fabricate the wafer such as an identification of the processing chamber of a multiple chamber processing tool. Tool data may also include process parameters such as hardware parameters used by a processing tool, processing tool maintenance history, and/or a specification of the material used in processing the wafer. In an embodiment, the wafer data is passed from the metrology tool 204 and includes the values obtained from the measurement of a wafer parameter. Manufacturing data may further include wafer IDs and/or product types associated with the wafers. The computer 202 may receive information from other systems used in the fabrication process such as a design database associated with the product type, a process control system, and/or other systems used to predict wafer parameters.

In the illustrated embodiment of the system 200, the computer 202 is connected to and sends information to the receiving computer 208a and the receiving fabrication tool 208. In an embodiment, the computer 202 is connected to and sends information to additional and/or different tools or systems used in the processing of semiconductor wafers or for data analysis. In an embodiment, the receiving computer 208a is included in the process control system. In an embodiment, the receiving computer 208a is operable to perform engineering analysis. The fabrication tool 208 is may be a CVD tool, a PVD tool, an etch tool, a thermal oxidation tool, an ion implantation tool, photolithography tool, and/or any other fabrication tool known in the art.

Figure 3A:
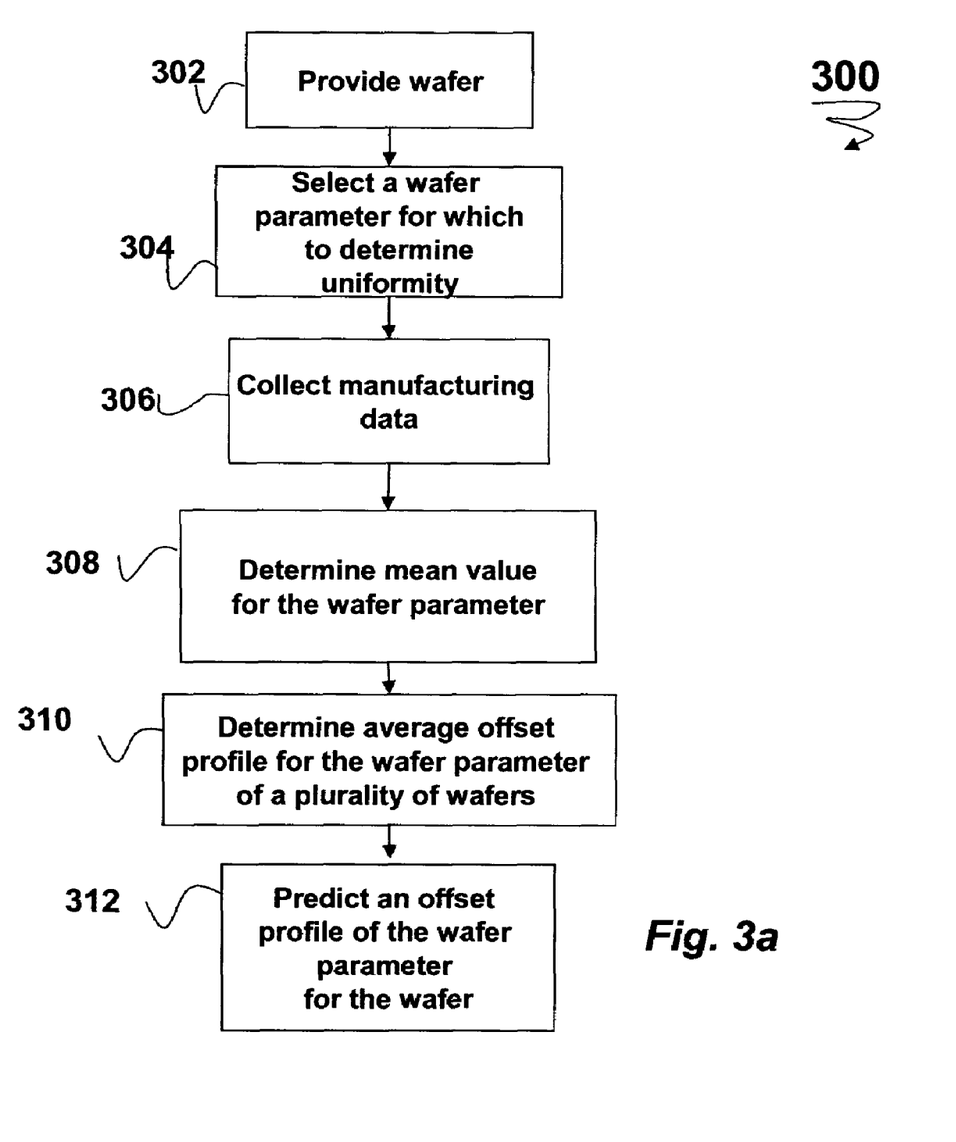
FIG. 3a is a flowchart illustrating an embodiment of a method for predicting the uniformity of a wafer.

Referring now to FIG. 3a, a method 300 for predicting the uniformity of a wafer is illustrated. The uniformity of a wafer may be predicted by predicting the offset profile for the wafer. The offset profile for a wafer includes, for a location on a wafer, a determination of the offset from a mean value for a selected wafer parameter. The offset profile for a wafer may include the offset from a mean value for the selected wafer parameter at one or a plurality of locations on the wafer. The method 300 begins at step 302 where a wafer, for which the uniformity is to be predicted, is provided. The wafer provided may be the wafer 100, described above with reference to FIG. 1. The wafer may be associated with a product type. The method proceeds to step 304 where a wafer parameter is selected. The wafer parameter selected is the wafer parameter of the wafer for which an offset profile will be generated. The selected wafer parameter may include a dimension of a feature such as the width of line, the width or depth of a trench, the width of a contact, the thickness of a layer, a critical dimension, and/or a variety of other wafer parameters known in the art and with a value that is capable of being determined by metrology tools during fabrication process. The selected parameter may not be determined at a location on the provided wafer by metrology tools during the fabrication process but instead predicted by the method 300. In an embodiment, the value of the selected parameter is determined by a metrology tool in the fabrication process for at least one location on the provided wafer, and the method 300 may predict the value of the selected parameter for at least one location on the wafer. In an embodiment, the selected wafer parameter is the thickness of a layer. In a further embodiment, the selected wafer parameter is the thickness of an interlayer dielectric layer (ILD). In an embodiment, the selected wafer parameter is the width of a feature.

The method 300 proceeds to step 306 where manufacturing data is collected. The manufacturing data may be collected by a computer such as the computer 202 of the system 200, described above in reference to FIG. 2. The manufacturing data collected includes data for the wafer provided in step 302. The manufacturing data collected also includes data for a plurality of wafers, the plurality of wafers being defined as a plurality of wafers exclusive of the wafer provided in step 302. In an embodiment, the plurality of wafers has been processed recently. In an embodiment, the plurality of wafers has been processed close in time to the wafer provided in step 302. The manufacturing data includes wafer data and tool data. The wafer data on the plurality of wafers may include the value of the selected parameter at one or more locations on a wafer. The locations may include locations such as, the locations 100a, 100b, 100c, 100d, and/or 100e, described above with reference to FIG. 1. In an embodiment, the value of the selected parameter includes the offset from the mean value of the selected parameter at the location. The tool data for the plurality of wafers and the wafer provided in step 302 may include a designation of the processing tool used. In an embodiment, this designation includes a designation of a particular processing chamber of a multiple chamber processing tool.

The method 300 then continues to step 308 where a mean value of the selected wafer parameter for the wafer provided in step 302 is determined. In an embodiment, the selected wafer parameter is the thickness of a layer, and the mean thickness of the layer of the wafer is determined. In an embodiment, the mean value of the selected wafer parameter is predicted. In the embodiment, the mean value of the wafer parameter may be predicted using regression methods and the manufacturing data collected in step 306. In an alternative embodiment, the mean value is determined by a metrology tool. In an embodiment of the method 300, step 308 is not performed and the mean value of the wafer parameter is not determined. In the embodiment, the method 300 may predict the uniformity of a wafer by determining the offset from a mean value of a wafer parameter at a location on a wafer without predicting the actual value of the wafer parameter at that location.

The method 300 then continues to step 310 where an average offset profile for a selected wafer parameter is determined. The average offset profile includes the average of the offset profiles of the selected wafer parameter that were determined for a plurality of wafers processed with a substantially similar process parameter as the provided wafer. In an embodiment, step 308 is performed by a computer such as the computer 202, described above with reference to FIG. 2. A process parameter is determined that may be correlative to the offset from the mean value of a selected wafer parameter at a location on the wafer. In an embodiment, a process parameter is correlative to the selected wafer parameter in that the offset from the mean of the selected wafer parameter at a location is substantially similar for those wafers processed using a substantially similar value of the process parameter. In an embodiment, the process parameter is correlative to the selected wafer parameter in that the offset from the mean of the wafer parameter at a location is different for wafers processed using different values of the process parameter. The correlative process parameter may be determined using manufacturing data of a plurality of wafers collected in step 306. The correlative process parameter may be selected using a variety of statistical analysis tools, for example, a score plot. In an embodiment, the correlative process parameter is the processing chamber of a multiple chamber processing tool. In the embodiment, the offset from the mean value of the wafer parameter may be substantially similar for those wafers processed using the same processing chamber. In the embodiment, the offset from the mean value of the wafer parameter may be substantially different for those wafers processed using different chambers. In an embodiment, the correlative process parameter is the chamber of a multiple chamber deposition tool such as a CVD tool.

The offset profiles for a plurality of wafers using substantially similar value of correlative process parameter as the wafer provided in step 302 are then determined using the collected manufacturing data. In an embodiment, the offset profiles for a plurality of wafers using a substantially similar value of correlative process parameter and being associated with the same product type as the provided wafer are determined. The offset profiles include, for one or more locations on a wafer, the offset from the mean value of the selected wafer parameter for a plurality of wafers. The average offset profile is calculated from the offset profiles for a plurality of wafers. To determine the average offset profile, the average offset from the mean value of the selected parameter may be determined for each location included in the offset profiles. The average offset of a location on the wafers may be determined by the use of a statistical tool. In an embodiment, the average offset at a location is determined by using a moving average of the measurements of the selected wafer parameter at that location on the wafer for a plurality of wafers. In an alternative embodiment, the average offset at a location is determined by using an exponentially weighted moving average (EWMA) of the measurements of the selected wafer parameter at that location on the wafer for a plurality of wafers.

The method 300 then continues to step 312 where an offset profile is predicted for the wafer provided in step 302. In an embodiment, the offset profile is predicted by a computer such as the computer 202, described above with reference to FIG. 2. The predicted offset profile includes the predicted offset from the mean value of the selected wafer parameter at one or more locations on the wafer. The offset profile is predicted by applying the average offset profile to the wafer. In an embodiment, after using the average offset profile determined in step 310 to predict the offset from the mean value, a prediction of the actual value of the selected wafer parameter at a location is determined by applying the mean value of the selected wafer parameter and the offset from the mean value of the selected wafer parameter. The offset and the mean may be summed to determine the actual value. In an embodiment, the offset from the mean value of the selected wafer parameter is determined by metrology equipment for at least one location on the provided wafer.

In an embodiment, the method 300 continues to further steps where the predicted offset profile for the wafer is fed-forward for use in determining future processing of the wafer. For example, the profile may be determined by the computer 202 of the system 200 and fed-forward to the receiving fabrication tool 208, described above in reference to FIG. 2. In an embodiment, the method 300 continues to further steps where the predicted offset profile is used for feed-back control of the process, for example, the profile may be fed-back to control a processing tool, such as the receiving fabrication tool 208, described above in reference to FIG. 1. In an embodiment, the offset profile may be fed-back to control a deposition tool. In an embodiment, the method 300 continues to further steps where the predicted offset profile for the wafer is used as a statistical process control monitor for the wafer. In an embodiment, the predicted offset profile is used to determine the need to rework the wafer. In an embodiment, the offset profile is sent to a computer, such as the receiving computer 208*a*, described above in reference to FIG. 2. In an embodiment, the profile is used by the computer to reduce process variation. In an embodiment, the method 300 may reduce the monitor wafers required for a fabrication process. In an embodiment, the method 300 predicts an offset profile for the selected wafer parameter for at least one wafer of a lot and for at least one wafer of the lot the selected wafer parameter is measured.

Figure 3B:
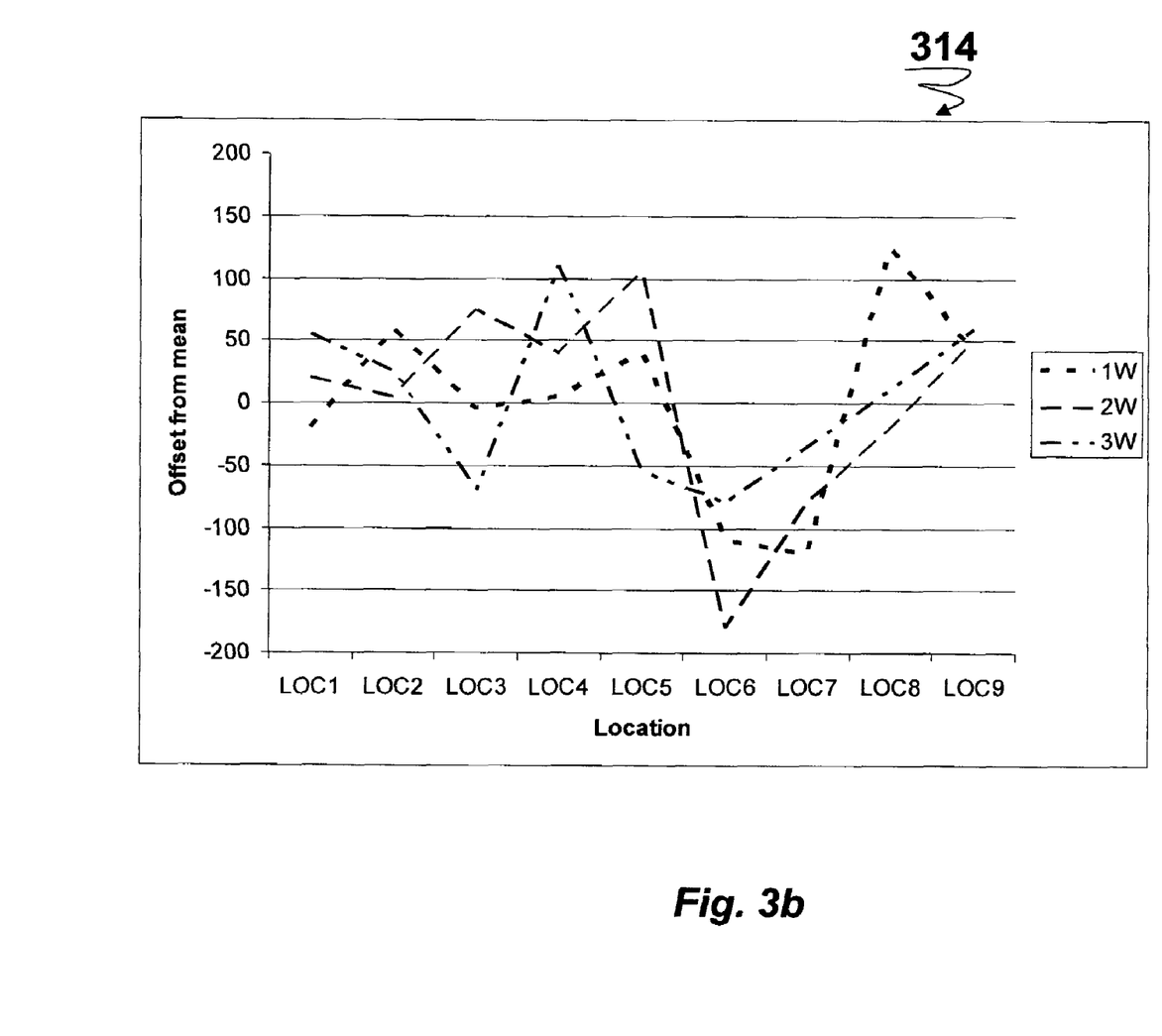

Referring now to FIGS. 3*a*, 3*b*, 3*c*, 3*d*, 3*e*, and 3*f*, an embodiment of the method 300 is illustrated. In the embodiment, a wafer associated with a product type is provided in step 302. The embodiment continues to step 304 where a wafer parameter is selected for determining the uniformity of the provided wafer. In the illustrated embodiment, the wafer parameter selected is the thickness of a layer. In an embodiment, the wafer parameter selected is the thickness of an ILD layer. In step 306, manufacturing data is collected on the provided wafer and a plurality of wafers. The plurality of wafers includes wafers associated with the product type of the provided wafer, and is exclusive of the provided wafer. FIG. 3*b* illustrates gathered wafer data for the plurality of wafers. The graph 314 includes, for the plurality of wafers 1W, 2W, and 3W, the offset from the mean layer thickness at a plurality of locations on the wafer. It is understood that only three wafers are being shown for the sake of example, and than many more wafers can be analyzed and graphed in a similar manner. The x-axis of the graph 314 includes the locations on the wafer LOC1, LOC2, LOC3, LOC4, LOC5, LOC6, LOC7, LOC8, and LOC9, the y-axis includes the offset from the mean layer thickness. In an embodiment, the units of offset is angstroms. In the illustrated embodiment, the layer thickness is determined at nine locations on each of the wafers. In an embodiment, the plurality of wafers included in the graph 314 are from a plurality of lots, with data from one or two wafers per lot of data collected.

Figure 3C:
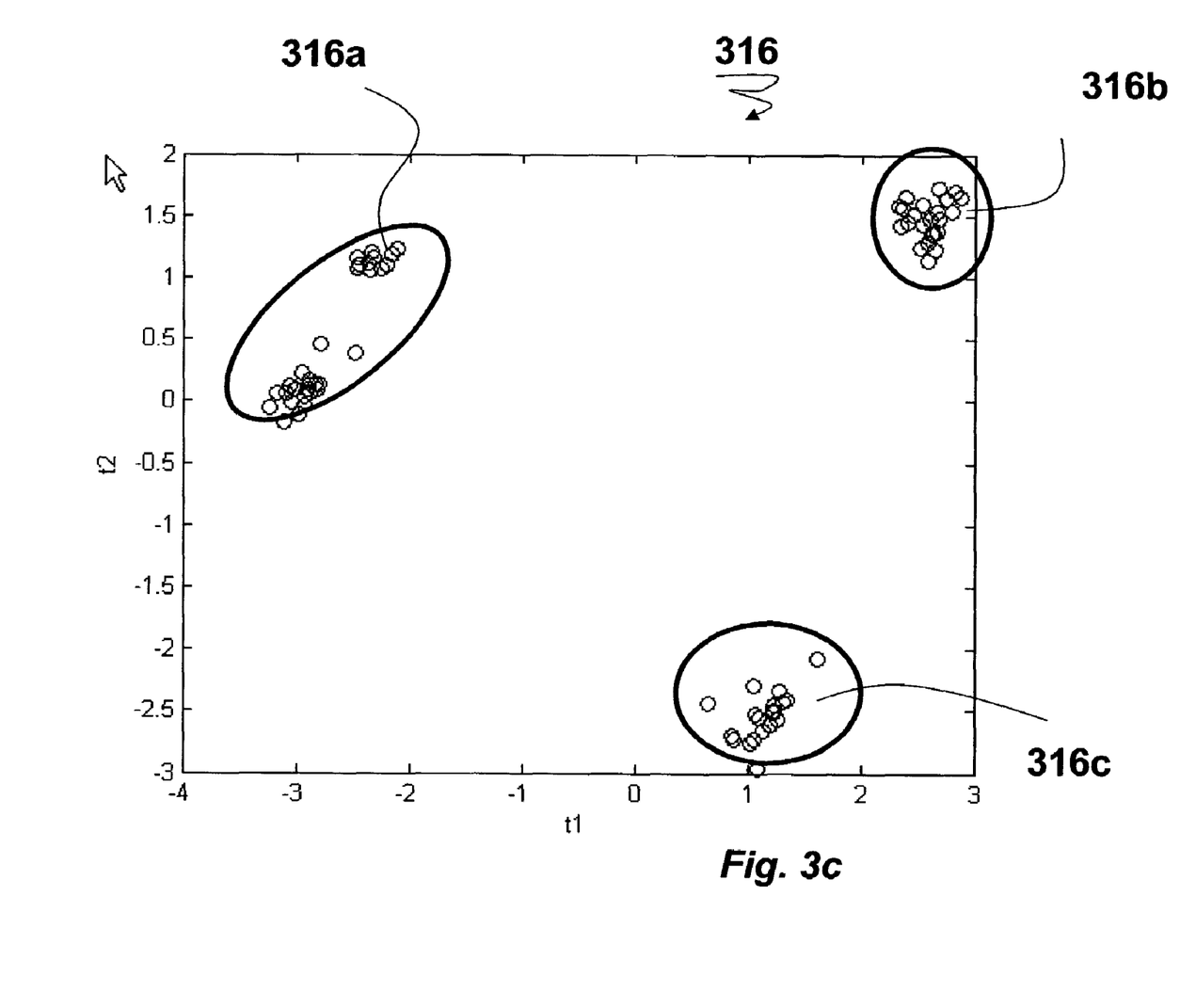
Figure 3D:
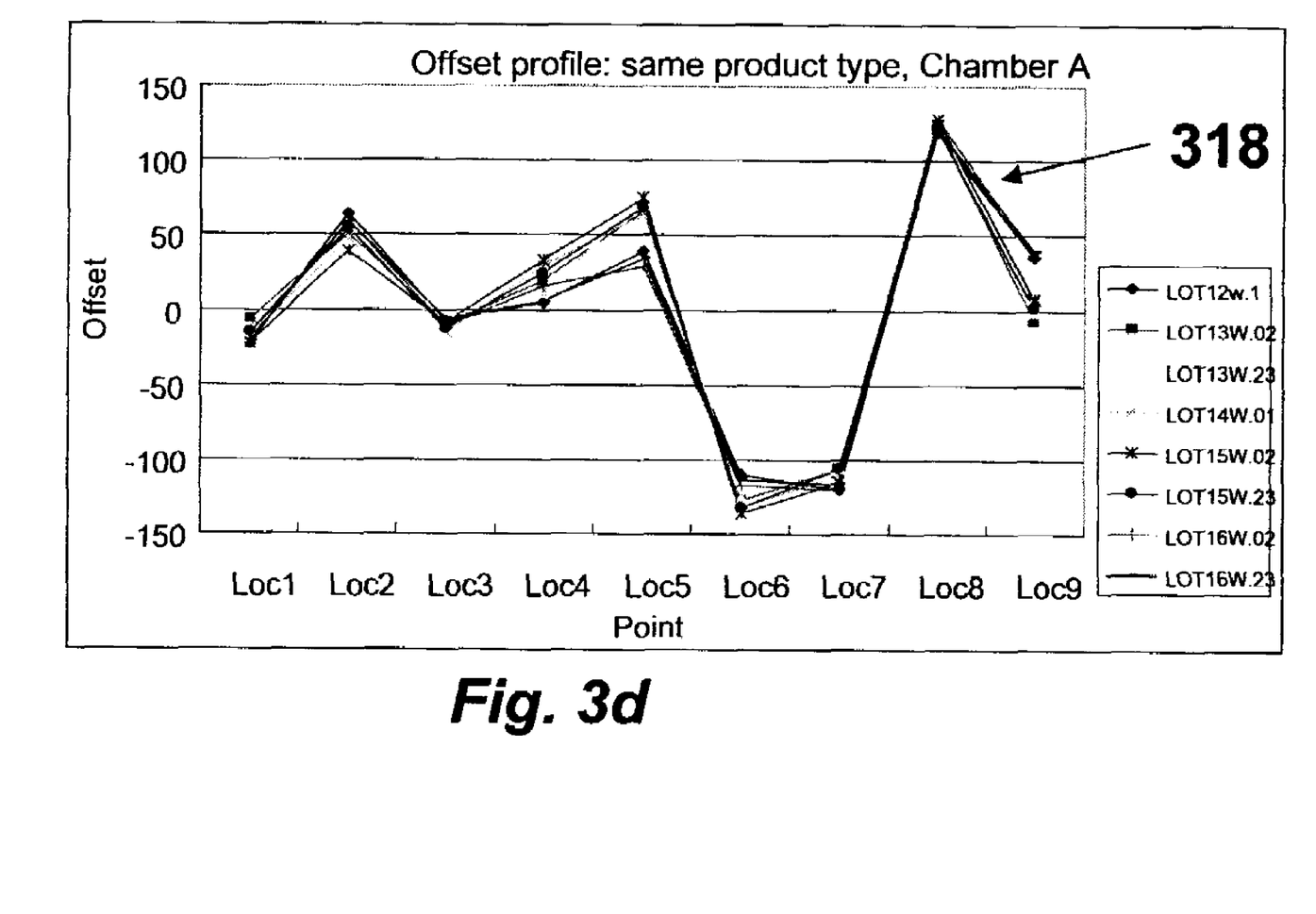

In the illustrated embodiment, step 308 is omitted from the method 300 and the embodiment continues to step 310 where an average offset profile for the layer thickness of a plurality of wafers is determined. In the illustrated embodiment, a correlative process parameter is determined by a score plot as illustrated in FIG. 3*c*. The score plot 316 is generated by plotting the offset from the mean thicknesses of a layer for the plurality of wafers. The score plot 316 illustrates the data points of the plotted thickness values are found in three areas designated as reference numbers 316*a*, 316*b*, and 316*c* respectively. The manufacturing data collected may be reviewed to find the process parameter that is the substantially similar for the wafers with data points within each area and different for the wafers in different areas. In the illustrated embodiment, the correlative process parameter is a processing chamber. In the illustrated embodiment, for a location on a wafer, there is a different offset from the mean layer thickness for wafers processed through different chambers and a similar offset from the mean layer thickness for wafers processed through the same chamber. The wafers represented by data points in the area 316a were processed using a processing chamber A. The wafers represented by data points in the area 316b were processed using processing chamber B. The wafers represented by data points in the area 316c were processed using processing chamber C. In an embodiment, the processing chambers A, B, and C are processing chambers of deposition tools. In a further embodiment, the processing chambers A, B, and C are processing chambers of CVD tools. In an embodiment, the wafer provided in step 302 was processed by the processing chamber A. FIG. 3d illustrates offset profiles 318 of layer thickness for a plurality of wafers associated with the product type of the provided wafer and processed in the processing chamber A.

Figure 3E:
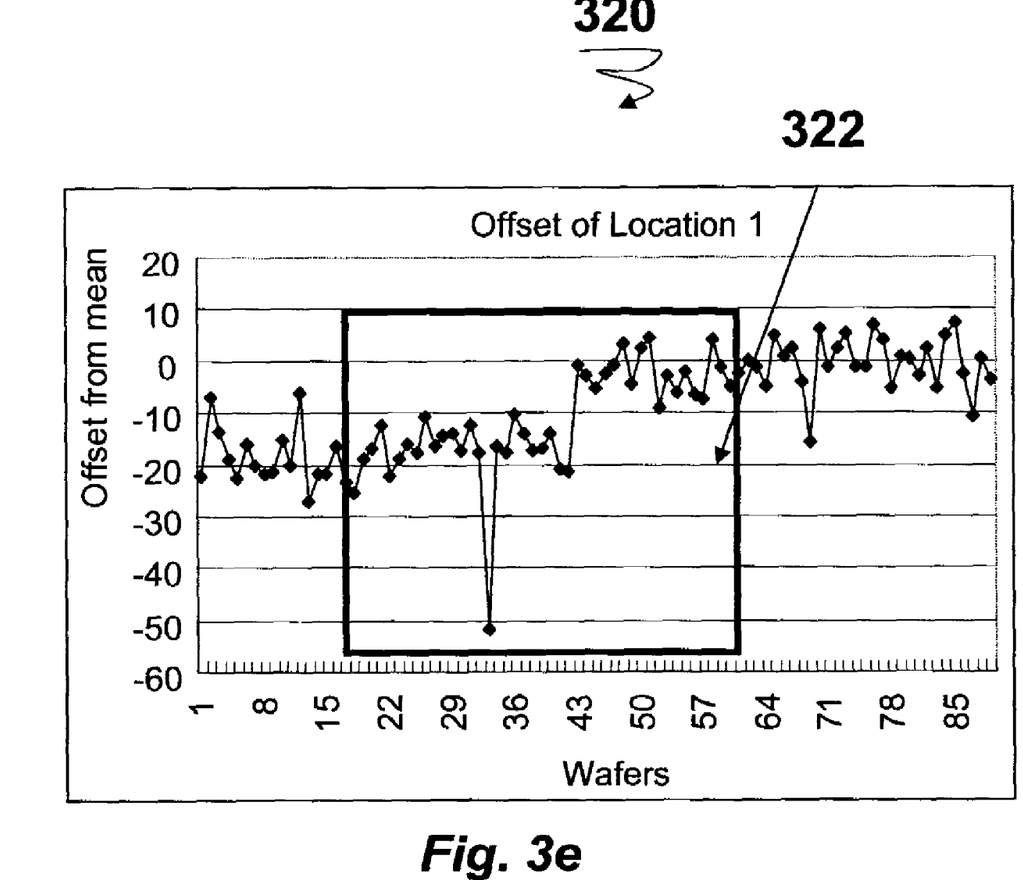
Figure 3F:
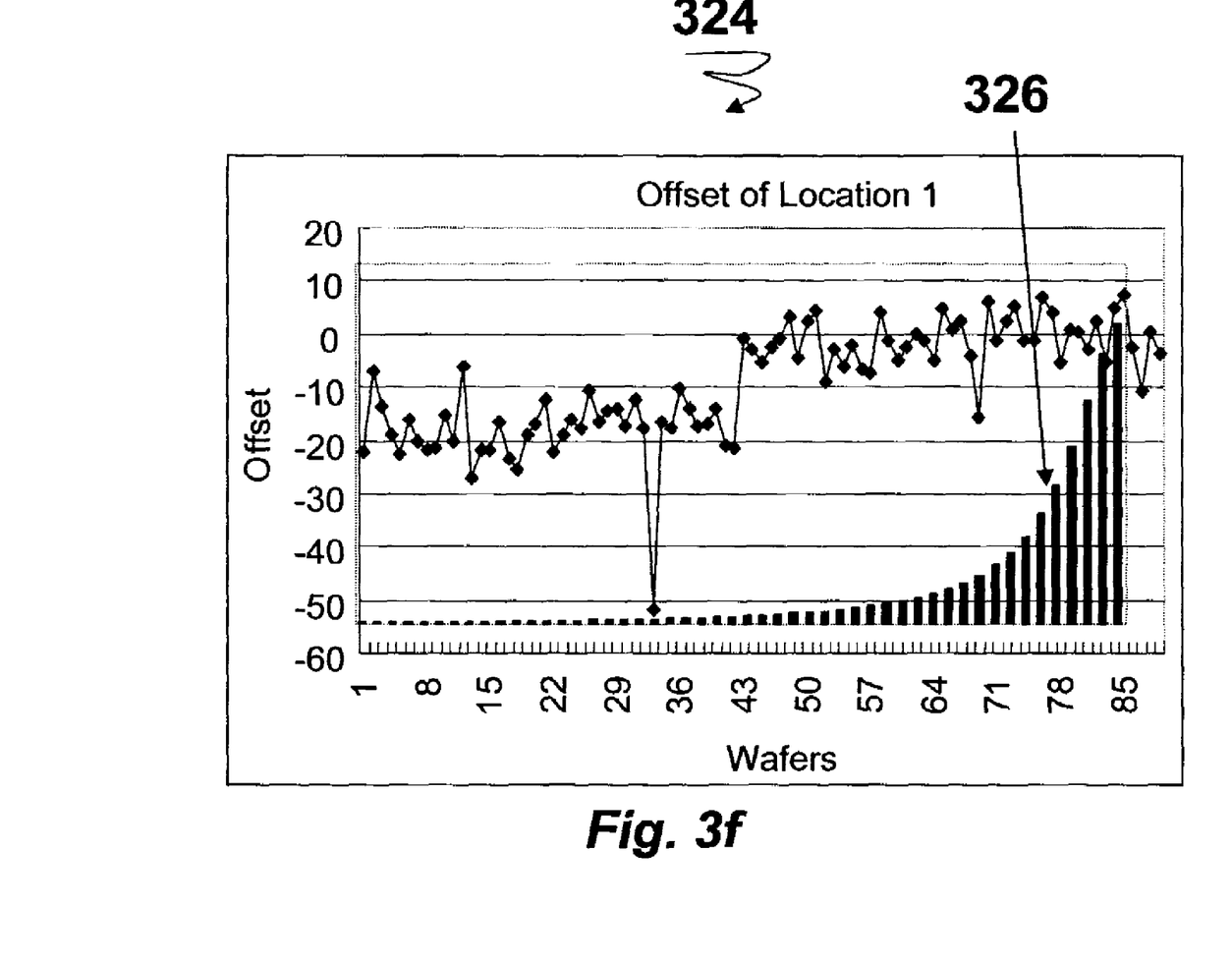

In the illustrated embodiment, an average offset profile of layer thickness for the plurality of wafers associated with the product type and processed in processing chamber A is determined from the plurality of offset profiles 318. In an embodiment, the average offset profile of the layer thickness is determined by a moving average, as illustrated in FIG. 3e. The graph 320 is generated from the manufacturing data including the determined offset from the mean value of the layer thickness for a location on a plurality of wafers. The average of the data points in a window 322 is determined. The size of the window 322 may be determined by the user of the method. The window 322 may move to include more recent data points and exclude more distant data points for determining the average for subsequent provided wafers. In an embodiment, the average offset of a wafer parameter at a location is determined by an EWMA as illustrated in FIG. 3f. The graph 324 is generated from the manufacturing data including the determined offset from the mean value the layer thickness for a location on a plurality of wafers. In using the EWMA method, the latest data points are weighted more heavily in determining the average (illustrated by the bar chart 326). The decay ratio of the embodiment illustrated is 0.5. The illustrated embodiment would then continue to determine the average for each of the nine locations provided by the manufacturing data. The average offset profile includes determined average at each of the nine locations. After determining the average offset profile, the method 300 continues as described above to predict an offset profile for the provided wafer. The offset profile predicted may include the predicted offset at nine locations on the provided wafer.

Figure 4:
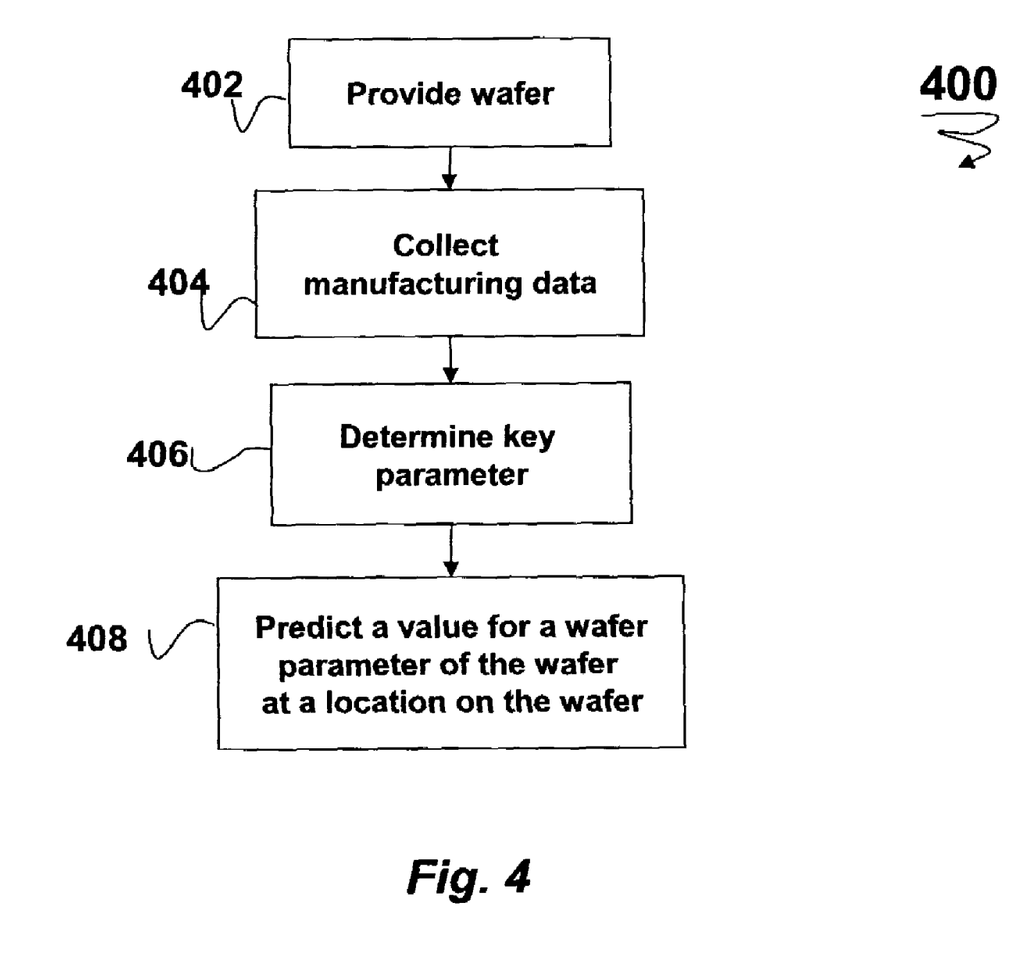
FIG. 4 is a flowchart illustrating an embodiment of a method for predicting the uniformity of a wafer.

Referring now to FIG. 4, an alternative method 400 can be used to predict the uniformity of a wafer. The method 400 begins at step 402 where a wafer, for which the uniformity is to be predicted, is provided. The wafer provided may be the wafer 100, described above with reference to FIG. 1. The method 400 may be used to predict a wafer parameter of a wafer at a plurality of locations on the wafer such as, locations 100a, 100b, 100c, 100d, and/or 100e of the wafer 100, also illustrated above in FIG. 1. In an embodiment, the wafer parameter predicted is the thickness of a layer such as an interlayer dielectric layer (ILD). In an embodiment, the wafer parameter predicted is the width of a feature. The method 400 proceeds to step 404 where manufacturing data is collected. The manufacturing data may be collected by a computer such as the computer 202 of the system 200, described above in reference to FIG. 2. The manufacturing data includes wafer data and tool data. The manufacturing data collected may include data for the wafer provided in step 402. The manufacturing data collected also includes data for a plurality of wafers exclusive of the wafer provided in step 402 on which the wafer parameter to be predicted for the provided wafer has been determined by metrology equipment.

The method 400 proceeds to step 406 where one or more key process parameters are determined. The determined key process parameter may be correlative to the wafer parameter to be predicted. In an embodiment, the determined key process parameter is correlative to the wafer parameter to be predicted at a specific location on the wafer. The determined key process parameter may differ depending on the location on the wafer for which the wafer parameter is predicted, such as the key process parameters determined for a wafer parameter at location 100a may differ from the key process parameters determined for the wafer parameter at location 100b, the locations 100a and 110b illustrated above in reference to FIG. 1. The key process parameter may be determined using regression methods. The determined key process parameter may form a basis of a regression equation to relate it to the wafer parameter to be predicted. The regression equation may include linear or nonlinear relations. In an embodiment, the determined key process parameter includes a designated chamber of a multiple chamber tool.

The method 400 proceeds to step 408 where the value for a wafer parameter of the provided wafer is predicted for one or more locations on the provided wafer. In an embodiment, the wafer parameter is predicted using a regression equation developed in step 406 and the manufacturing data of the provided wafer collected in step 404.

Although only a few exemplary embodiments of this invention have been described in detail above, those skilled in the art will readily appreciate that many modifications are possible in the exemplary embodiments without materially departing from the novel teachings and advantages of this disclosure.

In one embodiment, a method of monitoring uniformity of a wafer is provided. A wafer parameter is selected. Manufacturing data is collected. The manufacturing data includes measurements of the selected wafer parameter. An average offset profile of the wafer parameter for a first wafer and a second wafer is determined using the manufacturing data. The first wafer and the second wafer are associated with a product type and were processed by a processing tool. An offset profile for a third wafer is predicted for a wafer using the average offset profile. The third wafer is associated with the product type. The third wafer was processed by the processing tool.

In another embodiment, a method of semiconductor wafer processing is provided. A first wafer associated with a product type is provided. The first wafer is processed in a processing chamber. A mean value for a wafer parameter is determined for the first wafer. An average offset profile for the wafer parameter of a second wafer and a third wafer is determined. The second wafer and the third wafer are associated with the product type and were processed in the processing chamber. A value of the wafer parameter at a location on the first wafer is determined using the average offset profile and the mean value of the wafer parameter for the first wafer.

In another embodiment, a computer including a recordable medium is provided. Instructions are stored on the recordable medium for at least one routine. The routine is operable to receive manufacturing data. The routine is operable to determine an average offset profile for a wafer parameter using the manufacturing data. The routine is operable to predict the value of the wafer parameter for a wafer at a location on the wafer based on the average offset profile.

In another embodiment, an alternative method of monitoring uniformity of wafer is provided. Manufacturing data is collected, including a measurement result for a wafer parameter of a first and second wafer. A correlative process parameter for the wafer parameter is determined using the manufacturing data. A wafer parameter of a third wafer is predicted using the determined correlative process parameter. The prediction includes predicting the wafer parameter of the third wafer at a plurality of locations on the third wafer.

What is claimed is:

1. A method of monitoring uniformity of a wafer comprising:
   selecting a wafer parameter;
   collecting manufacturing data including a measurement of the wafer parameter for a first wafer and a second wafer, wherein the first wafer and the second wafer are associated with a product type and were processed by a processing tool;
   determining an average offset profile of the wafer parameter for the first wafer and the second wafer using the collected manufacturing data wherein the average offset profile includes an average offset from a mean value of the selected wafer parameter at a plurality of locations on the first wafer and the second wafer; and
   predicting an offset profile for a third wafer associated with the product type and processed by the processing tool using the determined average offset profile, wherein a computer comprising a recordable medium on which is stored instructions for at least one routine performs the determining the average offset profile and the predicting the offset profile.

2. The method of claim 1 wherein the processing tool is correlative to the wafer parameter.

3. The method of claim 1 wherein the wafer parameter is a dimension of a feature.

4. The method of claim 1 wherein the processing tool is a first chamber of a fabrication tool.

5. The method of claim 1 further comprising:
   using the predicted offset profile to determine subsequent processing of the third wafer.

6. The method of claim 1 further comprising:
   using the predicted offset profile to monitor a processing tool.

7. A method of semiconductor wafer processing comprising:
   providing a first wafer associated with a product type and processed in a processing chamber;
   determining a mean value of a wafer parameter for the first wafer;
   determining an average offset profile of the wafer parameter for a second wafer and a third wafer associated with the product type and processed in the processing chamber wherein the average offset profile includes an average offset from a mean value of the wafer parameter at a plurality of locations on the second wafer and the third wafer, and
   predicting a value of the wafer parameter at a location on the first wafer using the average offset profile and the mean value of the parameter for the first wafer; and
   using the predicted value of the wafer parameter to determine a process parameter for a fabrication process step; and
   performing said fabrication process step.

8. The method of claim 7 wherein the wafer parameter comprises a thickness of a layer.

9. The method of claim 8 wherein the layer comprises a dielectric layer.

10. The method of claim 7 wherein the processing chamber comprises a CVD chamber.

11. The method of claim 7 wherein the average offset profile is determined using at least one of an EWMA and a moving average.

12. The method of claim 7 wherein the determining the mean value of the wafer parameter includes predicting the mean value of the wafer parameter.

13. The method of claim 7 further comprising:
    predicting values for the wafer parameter at a plurality of locations on the first wafer.

14. The method of claim 7 wherein the first wafer is included in a lot of wafers, and wherein the lot of wafers includes a fourth wafer having the wafer parameter measured for at least one location.

15. A computer recordable medium on stored instructions when executed perform at least one routine operable to:
    receive manufacturing data;
    determine an average offset profile for a wafer parameter using the manufacturing data, wherein the average offset profile includes a first average value the wafer parameter is offset from a mean value at a first location of a wafer and a second average value the wafer parameter is offset from the mean value at a second location of a wafer; and
    predict the wafer parameter for a first wafer of a product type and processed in a processing chamber based on the determined average offset profile.

16. The computer of claim 15 further operable to:
    select a process parameter from the received manufacturing data, wherein the selected process parameter is correlative to the wafer parameter.

17. The computer of claim 15 wherein the determining the average offset profile includes determining an offset profile for a second wafer and determining an offset profile for a third wafer, wherein the second wafer and the third wafer are associated with the product type and processed in the processing chamber.

18. The method of claim 1, further comprising:
    sending the predicted offset profile for the third wafer to a fabrication tool;
    determining a process parameter for the fabrication tool; and
    performing a fabrication process step using the fabrication tool and the determined process parameter.

* * * * *